(12) United States Patent
Taylor

(10) Patent No.: US 6,589,959 B1
(45) Date of Patent: Jul. 8, 2003

(54) CRYSTALLINE BIS[(E)-7-[4-(4-FLUOROPHENYL)-6-ISOPROPYL-2-[METHYL(METHYLSULFONYL)AMINO]PYRIMIDIN-5-YL](3R,5S)-3,5-DIHYDROXYHEPT-6-ENOIC ACID] CALCIUM SALT

(75) Inventor: Nigel P Taylor, Macclesfield (GB)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 09/869,462

(22) PCT Filed: Dec. 23, 1999

(86) PCT No.: PCT/GB99/04439

§ 371 (c)(1),
(2), (4) Date: Jun. 28, 2001

(87) PCT Pub. No.: WO00/42024

PCT Pub. Date: Jul. 20, 2000

(30) Foreign Application Priority Data

Jan. 9, 1999 (GB) ................................................ 9900339

(51) Int. Cl.[7] .................... C07D 239/42; A61K 31/505; A61P 3/06
(52) U.S. Cl. ........................................ 514/275; 544/332
(58) Field of Search ............................ 544/332; 514/275

(56) References Cited

FOREIGN PATENT DOCUMENTS

EP         0 521 471         1/1993
WO         521471      *    6/1992

OTHER PUBLICATIONS

Watanabe M Et Al: "Synthesis and biological activity of methanesul fonamide pyrrole–substituted 3, 5–dihydroxy–6–heptenoates, a novel series of HMG–CoA reductase inhibitors" Bioorg. Med. Chem. (BMECEP, 09680896); 1997; vol. 5 (2); pp. 437–444, XP000882043 Shionogi and Company, Ltd.; Shionogi Res. Lab.; Osaka; 553; Japan (JP) see compound 3a and experimental.

Graul A Et Al: "ZD–4522. Hypolipidemic HMG–CoA reductase inhibitor" Drugs Future (DRFUD4, 03778282); 1999;vol. 24 (5); pp. 511–513, XP00882032 Prous Science; barcelona; 08080; Spain (ES) see especially description, p. 511.

\* cited by examiner

Primary Examiner—John M. Ford
Assistant Examiner—Hong Liu
(74) Attorney, Agent, or Firm—Morgan, Lewis & Bockius LLP

(57) ABSTRACT

The present invention relates to a crystalline form of the compound bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid]calcium salt, as well as processes for its manufacture and pharmaceutical compositions comprising the crystalline form, which is useful as an agent for treating hyperlipidemia, hypercholesterolemia and atherosclerosis.

2 Claims, 1 Drawing Sheet

Figure 1:
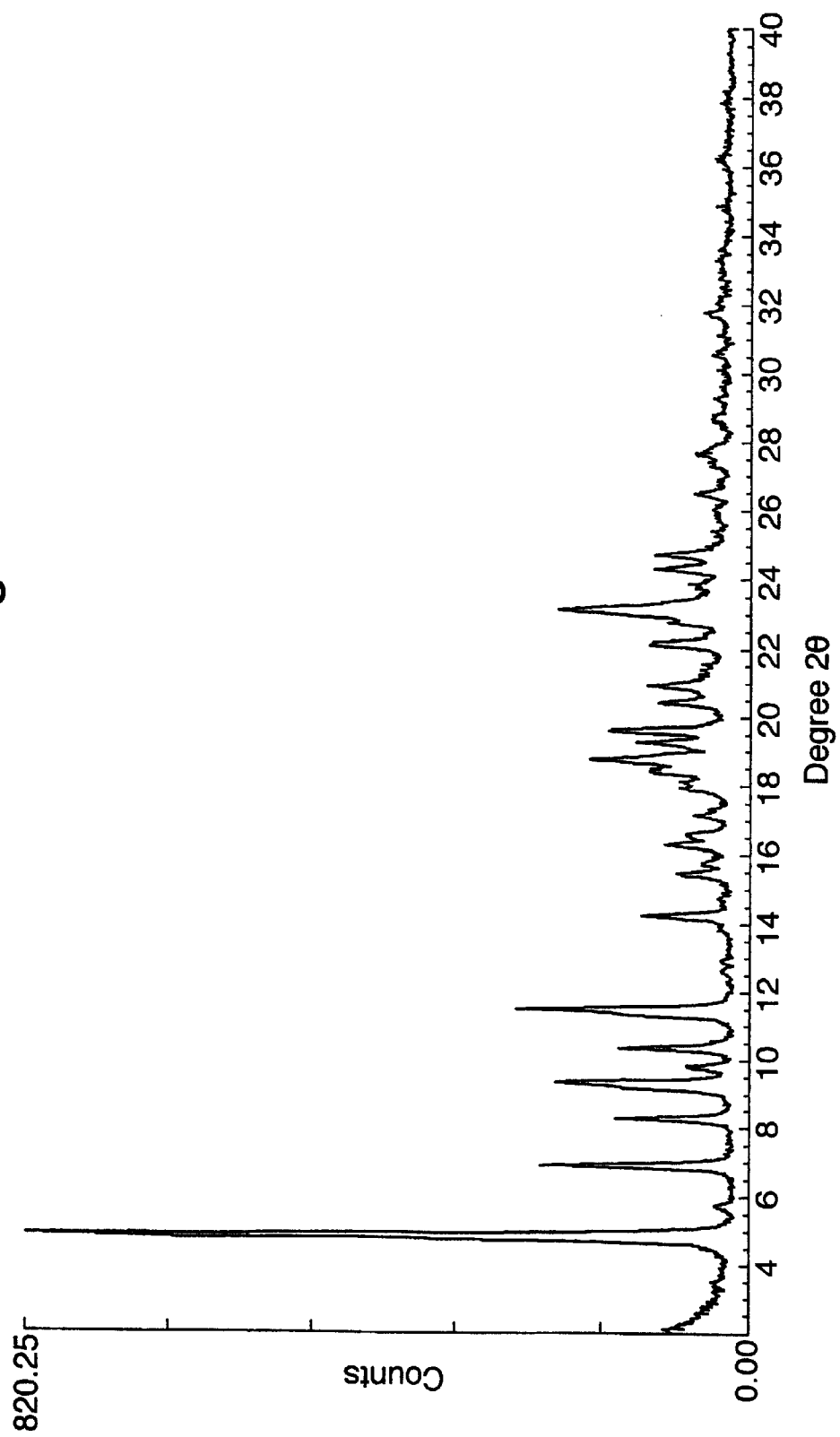

CRYSTALLINE BIS[(E)-7-[4-(4-FLUOROPHENYL)-6-ISOPROPYL-2-[METHYL(METHYLSULFONYL)AMINO]PYRIMIDIN-5-YL](3R,5S)-3,5-DIHYDROXYHEPT-6-ENOIC ACID] CALCIUM SALT

This application is the National Phase of International Application PCT/GB99/04439 filed Dec. 23, 1999 which designated the U.S. and that International Application was published under PCT Article 21(2) in English.

The present invention relates to a novel crystalline chemical compound and more particularly to a novel crystalline form of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid]calcium salt, hereinafter referred to as "the Agent", and illustrated in Formula I hereinafter, which compound is an inhibitor of the enzyme 3-hydroxy-3-methylglutaryl-coenzyme A reductase (HMG CoA reductase) and is useful as a pharmaceutical agent, for example in the treatment of hyperlipidemia, hypercholesterolemia and atherosclerosis, as well as other diseases or conditions in which HMG CoA reductase is implicated. The invention also relates to processes for the manufacture of the crystalline form, pharmaceutical compositions comprising the crystalline form and the use of the crystalline form in medical treatment.

European Patent Application, Publication No. 521471 (hereinafter EPA 521471), which is herein incorporated by reference, discloses an amorphous (powder) form of the Agent, prepared by dissolving the corresponding sodium salt in water, adding calcium chloride and collecting the resultant precipitate by filtration.

An amorphous form of a compound intended for pharmaceutical use may give rise to manufacturing problems and there is a need to identify crystalline forms of such compounds which have different physical characteristics compared to the amorphous form which may assist in the manufacture of the compound, or formulation of the compound, to the purity levels and uniformity required for regulatory approval. Crystalline forms of such compounds may also possess improved pharmacological characteristics, for example, improved bioavailability.

We have now surprisingly and unexpectedly discovered that the Agent can be prepared in a crystalline form.

According to the present invention there is provided a crystalline form of the Agent and hydrates thereof having an X-ray powder diffraction pattern with specific peaks at 2-theta=4.92, 11.50, 6.93, 9.35, 23.12 and 18.76° (hereinafter referred to as Form A).

The X-ray powder diffraction spectra was determined by mounting a sample of the crystalline form on Siemans single silicon crystal (SSC) wafer mounts and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5406 angstroms. The collimated x-ray source was passed through an automatic variable divergence slit set at V20 (20 mm path length) and the reflected radiation directed through a 2 mm antiscatter slit and a 0.2 mm detector slit. The sample was exposed for 4 seconds per 0.02 degree 2-theta increment (continuous scan mode) over the range 2 degrees to 40 degrees 2-theta in theta-theta mode. The running time was 2 hours 6 minutes and 40 seconds. The instrument was equipped with a scintillation counter as detector. Control and data capture was by means of a DECpc LPv 433sx personal computer running with Diffrac AT (Socabim) software.

The X-ray powder diffraction spectra of a typical sample of Form A is shown in FIG. 1 hereinafter. It will be understood that the 2-theta values of the X-ray powder diffraction pattern may vary slightly from one machine to another or from one sample of Form A to another, and so the values quoted are not to be construed as absolute.

Typically Form A is obtained in a hydrated form with, for example, a water content of about 7% w/w.

A further aspect of the present invention comprises a process for the preparation of Form A wherein Form A is caused to crystallise from a mixture of the Agent, water and one or more organic solvents. The optimum ratio of organic solvents and water in the mixture to obtain Form A is dependent on the characteristics of the organic solvents used and the process conditions employed. The precise conditions may be empirically determined. For example, Form A may be obtained by suspending the amorphous form of the Agent in water containing a co-solvent, such as acetonitrile, acetone or a mixture of methanol and methyl tert-butyl ether (MTBE), warming the mixture to obtain complete solution and then allowing the solution to cool, followed by isolation of Form A, such as by filtration. Suitable mixtures of water and co-solvent include, for example, 1:1 water/acetonitrile, 1:1 water/acetone and 1:1:1 water/methanol/MTBE, the ratios given being by volume. The amorphous form of the Agent to be used as starting material for the manufacture of Form A may be obtained, for example, as described in EPA 521471.

The utility of the compound of the invention may be demonstrated by standard tests and clinical studies, including those described in EPA 521471.

According to a further feature of the invention is a method of treating a disease condition wherein inhibition of HMG CoA reductase is beneficial which comprises administering to a warm-blooded mammal an effective amount of the Agent. The invention also relates to the use of Form A in the manufacture of a medicament for use in a disease condition.

The compound of the invention may be administered to a warm-blooded animal, particularly a human, in need thereof for treatment of a disease in which HMG CoA reductase is implicated, in the form of a conventional pharmaceutical composition. Therefore in another aspect of the invention, there is provided a pharmaceutical composition comprising Form A in admixture with a pharmaceutically acceptable carrier.

Such compositions may be administered in standard manner for the disease condition that it is desired to treat, for example by oral, topical, parenteral, buccal, nasal, vaginal or rectal administration or by inhalation. For these purposes the Agent may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solution or suspensions or sterile emulsions. A preferred route of administration is oral. The Agent will be administered to humans at a daily dose in, for example, the ranges set out in EPA 521471. The daily doses may be given in divided doses as necessary, the precise amount of the Agent received and the route of administration depending on the weight, age and sex of the patient being treated and on the particular disease condition being treated according to principles known in the art.

According to a further feature of the invention, there is provided a process for the manufacture of a pharmaceutical composition containing Form A as active ingredient, which comprises admixing Form A together with a pharmaceutically acceptable carrier.

The invention will now be illustrated by the following non-limiting Example.

EXAMPLE 1

Amorphous form of the Agent (465 mg) was added to a mixture of water (5 ml) and acetonitrile (5 ml) at 15° C. The mixture was warmed to 40° C. to obtain complete solution. The mixture was then cooled slowly to ambient temperature and stirred for 16 hours. The crystalline product was separated by filtration at ambient temperature and dried at 50° under vacuum to give Form A (337 mg) as white crystals.

X-ray powder diffraction (XRD):

| Peak Number | 2θ | d-Spacing | Counts/sec | Relative Intensity (>20%) |
|---|---|---|---|---|
| 1 | 4.92 | 17.945 | 820.25 | 100 |
| 2 | 11.50 | 7.686 | 258.75 | 31.55 |
| 3 | 6.93 | 12.750 | 230.25 | 28.07 |
| 4 | 9.35 | 9.455 | 213.75 | 26.06 |
| 5 | 23.12 | 3.843 | 212.75 | 25.94 |
| 6 | 18.76 | 4.726 | 177.5 | 21.64 |

Water content 7.1% w/w

[1]NMR (d[6]-DMSO) δ: 7.7 (2H, t), 7.3 (2H, t), 6.5 (1H, d), 5.5 (1H,dd), 4.2 (1H, m), 3.8 (1H, m), 3.5 (3H, s), 1.9–2.1 (2H, dd), 1.3–1.5 (2H, m), 1.2 (6H, d)

Mass Spectrum: MH+482.3

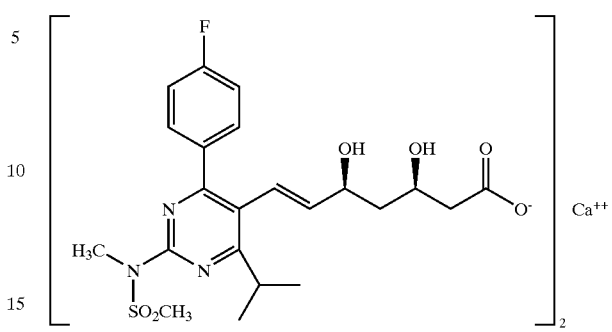

Formula I

What is claimed is:

1. A crystalline form of the compound bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid]calcium salt of the formula I

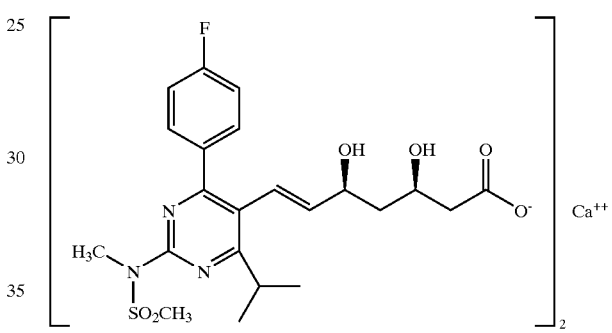

I in hydrated form having an X-ray powder diffraction pattern with specific peaks at 2-theta (2θ)=4.92, 11.50, 6.93, 9.35, 23.12 and 18.76°.

2. A pharmaceutical composition comprising the crystalline form of compound as claimed in claim 1, together with a pharmaceutically acceptable carrier.

* * * * *